(12) United States Patent
Haefner

(10) Patent No.: US 7,566,318 B2
(45) Date of Patent: Jul. 28, 2009

(54) ULTRASONIC SUBCUTANEOUS DISSECTION TOOL INCORPORATING FLUID DELIVERY

(75) Inventor: Paul A Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 687 days.

(21) Appl. No.: 10/653,456

(22) Filed: Sep. 2, 2003

(65) Prior Publication Data

US 2004/0204728 A1 Oct. 14, 2004

Related U.S. Application Data

(60) Provisional application No. 60/462,272, filed on Apr. 11, 2003.

(51) Int. Cl.
*A61B 17/20* (2006.01)

(52) U.S. Cl. .......................................... 604/22

(58) Field of Classification Search ............. 604/20–22, 604/118; 606/127, 128, 161, 162
See application file for complete search history.

(56) References Cited

U.S. PATENT DOCUMENTS

| 3,941,122 | A | * | 3/1976 | Jones .......................... 606/128 |
| 4,146,029 | A | | 3/1979 | Ellinwood |
| 4,506,680 | A | | 3/1985 | Stokes |
| 4,562,841 | A | | 1/1986 | Brockway et al. |
| 4,819,661 | A | | 4/1989 | Heil, Jr. et al. |
| 4,819,662 | A | | 4/1989 | Heil, Jr. et al. |
| 4,953,551 | A | | 9/1990 | Mehra et al. |
| 5,020,544 | A | | 6/1991 | Dahl et al. |
| 5,036,849 | A | | 8/1991 | Hauck et al. |
| 5,041,107 | A | | 8/1991 | Heil, Jr. et al. |
| 5,133,353 | A | | 7/1992 | Hauser |
| 5,170,784 | A | | 12/1992 | Ramon et al. |
| 5,179,945 | A | | 1/1993 | Van Hofwegen et al. |
| 5,203,348 | A | | 4/1993 | Dahl et al. |
| 5,209,229 | A | | 5/1993 | Gilli |
| 5,230,337 | A | | 7/1993 | Dahl et al. |
| 5,261,400 | A | | 11/1993 | Bardy |
| 5,282,785 | A | | 2/1994 | Shapland et al. |

(Continued)

FOREIGN PATENT DOCUMENTS

WO    WO 92/20402    11/1992

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—Matthew F Desanto
(74) *Attorney, Agent, or Firm*—Hollingsworth & Funk, LLC

(57) ABSTRACT

Ultrasonic dissection instruments and methods provide for fluid delivery during subcutaneous dissection. An ultrasonic dissection tool includes a handle, a transducer and a dissecting member. The dissecting member extends from the distal end of the transducer, and a fluid channel system extends from at least the proximal end to the distal end of the dissecting member. The fluid channel system terminates in a port system. The port system may include one or more apertures, one or more channels, and be adapted to transport fluids such as, for example, irrigation fluids, fluids having analgesics, antibiotics, and combinations of fluids and agents.

13 Claims, 9 Drawing Sheets

U.S. PATENT DOCUMENTS

| | | | |
|---|---|---|---|
| 5,284,136 | A | 2/1994 | Hauck et al. |
| 5,292,338 | A | 3/1994 | Bardy |
| 5,300,106 | A | 4/1994 | Dahl et al. |
| 5,301,677 | A | 4/1994 | Hsung |
| 5,313,953 | A | 5/1994 | Yomtov et al. |
| 5,314,430 | A | 5/1994 | Bardy |
| 5,314,459 | A | 5/1994 | Swanson et al. |
| 5,331,966 | A | 7/1994 | Bennett et al. |
| 5,360,442 | A | 11/1994 | Dahl et al. |
| 5,366,496 | A | 11/1994 | Dahl et al. |
| 5,372,606 | A | 12/1994 | Lang et al. |
| 5,376,106 | A | 12/1994 | Stahmann et al. |
| 5,388,578 | A | 2/1995 | Yomtov et al. |
| 5,391,200 | A | 2/1995 | KenKnight et al. |
| 5,397,342 | A | 3/1995 | Heil, Jr. et al. |
| 5,405,362 | A | 4/1995 | Kramer et al. |
| 5,411,031 | A | 5/1995 | Yomtov |
| 5,411,525 | A | 5/1995 | Swanson et al. |
| 5,411,539 | A | 5/1995 | Neisz |
| 5,439,482 | A | 8/1995 | Adams et al. |
| 5,441,518 | A | 8/1995 | Adams et al. |
| 5,445,608 | A | 8/1995 | Chen |
| 5,449,370 | A | 9/1995 | Vaitekunas |
| 5,468,254 | A | 11/1995 | Hahn et al. |
| 5,531,779 | A | 7/1996 | Dahl et al. |
| 5,545,202 | A | 8/1996 | Dahl et al. |
| 5,603,732 | A | 2/1997 | Dahl et al. |
| 5,620,466 | A | 4/1997 | Haefner et al. |
| 5,628,730 | A | 5/1997 | Shapland et al. |
| 5,634,938 | A | 6/1997 | Swanson et al. |
| 5,641,326 | A | 6/1997 | Adams |
| 5,662,688 | A | 9/1997 | Haefner et al. |
| 5,697,953 | A | 12/1997 | Kroll et al. |
| 5,704,365 | A | 1/1998 | Albrecht et al. |
| 5,724,984 | A | 3/1998 | Arnold et al. |
| 5,749,909 | A | 5/1998 | Schroeppel et al. |
| 5,807,306 | A | 9/1998 | Walsh |
| 5,827,326 | A | 10/1998 | Kroll et al. |
| 5,843,017 | A | 12/1998 | Yoon |
| 5,895,414 | A | 4/1999 | Sanchez-Zambrano |
| 5,916,243 | A | 6/1999 | KenKnight et al. |
| 5,957,956 | A | 9/1999 | Kroll et al. |
| 5,989,208 | A * | 11/1999 | Nita ............................ 604/22 |
| 5,997,497 | A * | 12/1999 | Nita et al. ..................... 604/22 |
| 6,044,298 | A | 3/2000 | Salo et al. |
| 6,055,454 | A | 4/2000 | Heemels |
| 6,099,567 | A | 8/2000 | Badylak et al. |
| 6,134,470 | A | 10/2000 | Hartlaub |
| 6,144,879 | A | 11/2000 | Gray |
| 6,148,230 | A | 11/2000 | KenKnight |
| 6,167,305 | A | 12/2000 | Cammilli et al. |
| 6,178,349 | B1 | 1/2001 | Kieval |
| 6,214,017 | B1 * | 4/2001 | Stoddard et al. ............ 606/128 |
| 6,280,462 | B1 | 8/2001 | Hauser et al. |
| 6,282,444 | B1 | 8/2001 | Kroll et al. |
| 6,295,474 | B1 | 9/2001 | Munshi |
| 6,304,786 | B1 | 10/2001 | Heil, Jr. et al. |
| 6,309,355 | B1 | 10/2001 | Cain et al. |
| 6,322,532 | B1 | 11/2001 | D'Sa et al. |
| 6,352,544 | B1 | 3/2002 | Spitz |
| 6,361,531 | B1 | 3/2002 | Hissong |
| 6,361,780 | B1 | 3/2002 | Ley et al. |
| 6,413,216 | B1 | 7/2002 | Cain et al. |
| 6,416,510 | B1 | 7/2002 | Altman et al. |
| 6,436,068 | B1 | 8/2002 | Bardy |
| 6,438,410 | B2 | 8/2002 | Hsu et al. |
| 6,500,121 | B1 | 12/2002 | Slayton et al. |
| 6,512,940 | B1 | 1/2003 | Brabec et al. |
| 6,522,915 | B1 | 2/2003 | Ceballos et al. |
| 6,524,251 | B2 * | 2/2003 | Rabiner et al. .............. 600/439 |
| 6,564,106 | B2 | 5/2003 | Guck et al. |
| 6,607,509 | B2 | 8/2003 | Bobroff et al. |
| 6,615,083 | B2 | 9/2003 | Kupper |
| 6,622,046 | B2 | 9/2003 | Fraley et al. |
| 6,695,781 | B2 * | 2/2004 | Rabiner et al. .............. 600/439 |
| 6,837,888 | B2 | 1/2005 | Ciarrocca et al. |
| 6,958,040 | B2 * | 10/2005 | Oliver et al. ................. 600/439 |
| 7,018,391 | B2 | 3/2006 | Spitz et al. |
| 7,190,997 | B1 | 3/2007 | Darvish et al. |
| 7,204,820 | B2 * | 4/2007 | Akahoshi ...................... 604/22 |
| 2002/0035376 | A1 | 3/2002 | Bardy et al. |
| 2002/0035377 | A1 | 3/2002 | Bardy et al. |
| 2002/0035378 | A1 | 3/2002 | Bardy et al. |
| 2002/0035379 | A1 | 3/2002 | Bardy et al. |
| 2002/0035380 | A1 | 3/2002 | Rissmann et al. |
| 2002/0035381 | A1 | 3/2002 | Bardy et al. |
| 2002/0042629 | A1 | 4/2002 | Bardy et al. |
| 2002/0042630 | A1 | 4/2002 | Bardy et al. |
| 2002/0042634 | A1 | 4/2002 | Bardy et al. |
| 2002/0049475 | A1 | 4/2002 | Bardy et al. |
| 2002/0049476 | A1 | 4/2002 | Bardy et al. |
| 2002/0052636 | A1 | 5/2002 | Bardy et al. |
| 2002/0068958 | A1 | 6/2002 | Bardy et al. |
| 2002/0072773 | A1 | 6/2002 | Bardy et al. |
| 2002/0082658 | A1 | 6/2002 | Heinrich et al. |
| 2002/0091414 | A1 | 7/2002 | Bardy et al. |
| 2002/0095184 | A1 | 7/2002 | Bardy et al. |
| 2002/0103510 | A1 | 8/2002 | Bardy et al. |
| 2002/0107544 | A1 | 8/2002 | Ostroff et al. |
| 2002/0107545 | A1 | 8/2002 | Rissmann et al. |
| 2002/0107546 | A1 | 8/2002 | Ostroff et al. |
| 2002/0107547 | A1 | 8/2002 | Erlinger et al. |
| 2002/0107548 | A1 | 8/2002 | Bardy et al. |
| 2002/0107549 | A1 | 8/2002 | Bardy et al. |
| 2002/0107559 | A1 | 8/2002 | Sanders et al. |
| 2002/0120299 | A1 | 8/2002 | Ostroff et al. |
| 2002/0193784 | A1 | 12/2002 | McHale et al. |
| 2003/0004546 | A1 | 1/2003 | Casey |
| 2003/0004552 | A1 | 1/2003 | Plombon et al. |
| 2003/0023175 | A1 | 1/2003 | Arzbaecher et al. |
| 2003/0032943 | A1 | 2/2003 | Topaz |
| 2003/0036778 | A1 | 2/2003 | Ostroff et al. |
| 2003/0040698 | A1 | 2/2003 | Makin et al. |
| 2003/0045904 | A1 | 3/2003 | Bardy et al. |
| 2003/0069609 | A1 | 4/2003 | Thompson |
| 2003/0073949 | A1 | 4/2003 | Giammarusti |
| 2003/0088278 | A1 | 5/2003 | Bardy et al. |
| 2003/0088279 | A1 | 5/2003 | Rissmann et al. |
| 2003/0088280 | A1 | 5/2003 | Ostroff |
| 2003/0088281 | A1 | 5/2003 | Ostroff et al. |
| 2003/0088282 | A1 | 5/2003 | Ostroff |
| 2003/0088283 | A1 | 5/2003 | Ostroff |
| 2003/0088286 | A1 | 5/2003 | Ostroff et al. |
| 2003/0097153 | A1 | 5/2003 | Bardy et al. |
| 2003/0212436 | A1 | 11/2003 | Brown |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT)Model of a Fully Subcutaneous ICD System*, Europace Supplements, vol. 2, Jun. 2001 at B83.

Stirbis et al., *Optmizing the Shape of Implanted Artificial Pacemakers,* Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve,* PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma,* PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children,* J. of Cardiovascular Electrophysiology, vol. 12, No. 3, pp. 356-360 (Mar. 2001).

* cited by examiner

ULTRASONIC SUBCUTANEOUS DISSECTION TOOL INCORPORATING FLUID DELIVERY

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to ultrasonic surgical instruments and, more particularly, to subcutaneous ultrasonic dissection instruments incorporating pharmacological delivery.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Implantable cardioverter/defibrillators (ICDs) have been used as an effective treatment for patients with serious cardiac arrhythmias. For example, a typical ICD includes one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators due to the difficulty of the implantation procedure. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that can safely undergo the required endocardial or epicardial lead/electrode implant procedure.

For reasons stated above, and for other reasons that will become apparent to those skilled in the art upon reading the present specification, there is a need for systems and methods that improve delivery of cardiac sensing and therapy leads/electrodes. There is a particular need for tools and techniques that facilitate implantation of such systems. The present invention fulfills these and other needs, and addresses deficiencies in known systems and techniques.

SUMMARY OF THE INVENTION

The present invention is directed to ultrasonic subcutaneous dissection tools, methods and systems that, in general, provide access for deployment of subcutaneous electrodes, cans, and housings used in cardiac monitoring, transthoracic defibrillation therapies, transthoracic pacing therapies, or a combination of the above. Embodiments of the present invention include ultrasonic subcutaneous dissection tools, and systems that include pharmacological delivery during dissection.

According to one embodiment, an ultrasonic dissection tool of the present invention includes a handle having a proximal end and a distal end, a transducer adapted to produce ultrasonic energy, and an elongated dissecting member having a proximal end and a distal end. The elongated dissecting member extends from the distal end of the transducer. A fluid channel system extends from at least the proximal end of the elongated dissecting member to the distal end of the elongated dissecting member. The fluid channel system terminates in a port system. The port system may include one or more apertures, one or more channels, and be adapted to transport fluids such as, for example, irrigation fluids, fluids having analgesics, antibiotics, and combinations of fluids and agents. The fluid dispensed through the fluid channel system is typically a liquid, but may alternatively be a gas. A system incorporating dissection tools in accordance with the present invention may include fluid storage, a pump, and tubing for fluid delivery.

Another embodiment of the present invention is directed to a sheath removably surrounding the dissector. The sheath may be left in place after removal of the dissector to facilitate electrode delivery and implantation. The sheath may thereafter be stripped out of the dissection path to fix the electrode lead, such as through the use of a peel-away feature.

Another embodiment of the present invention provides a method of dissection. The method of dissecting subcutaneous tissue in accordance with the present invention is directed to ultrasonically dissecting subcutaneous tissue with the dissection tool, and delivering a fluid from the dissection tool during dissection. The fluid delivered may include agents that provide analgesia, hemostasis, bacterial fighting and infection fighting, and/or flushing of debris. The dissection method may include steps of following the subcutaneous plane for dissection along the curvature of the rib cage, for example.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
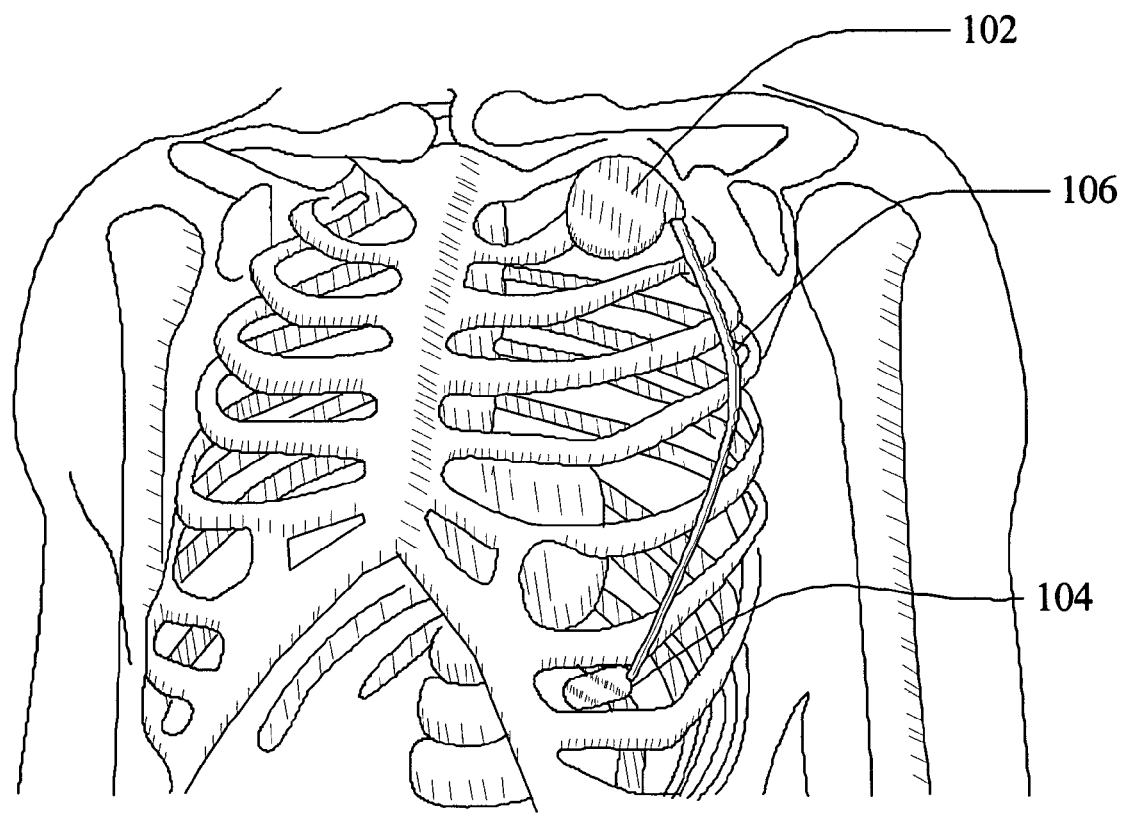
FIGS. 1A and 1B are views of a transthoracic cardiac sensing and/or stimulation device as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

A device in accordance with the present invention may include one or more of the features, structures, methods, or combinations thereof described herein below. For example, a subcutaneous ultrasonic dissector or dissection method may be implemented to include one or more of the advantageous features and/or processes described below. It is intended that such a dissection device or method need not include all of the features and functions described herein, but may be implemented to include selected features and functions that provide for unique structures and/or functionality.

In general terms, a dissection tool of the present invention may be used to facilitate implantation of a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart. A dissection tool and methodology of the present invention may be used to provide electrode and device access at various subcutaneous body locations.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature. In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Figure 1B:
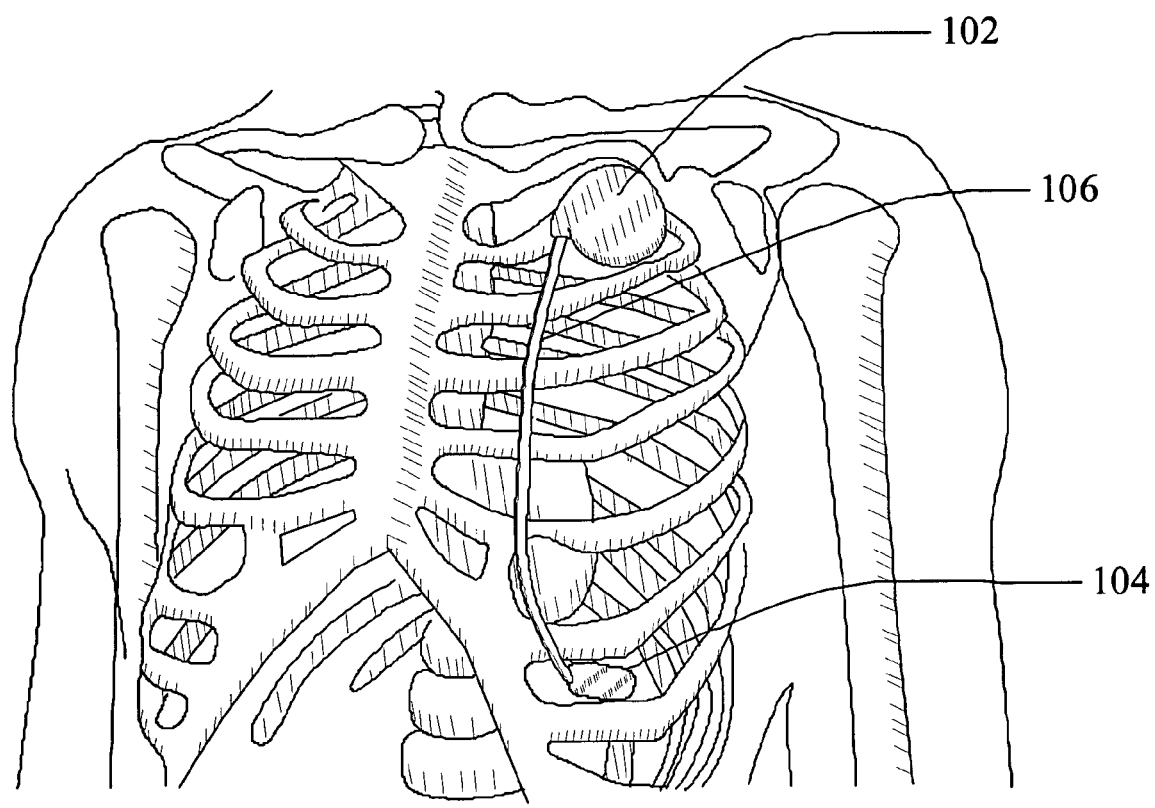

Referring now to FIGS. 1A and 1B of the drawings, there is shown a configuration of an ITCS device implanted in the chest region of a patient at different locations by use of a dissection tool of the present invention. In the particular configuration shown in FIGS. 1A and 1B, the ITCS device includes a housing 102 within which various cardiac sensing, detection, processing, and energy delivery circuitry may be housed. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed. An ITCS system according to this approach is distinct from conventional approaches in that it is preferably configured to include a combination of two or more electrode subsystems that are implanted subcutaneously in the anterior thorax.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and the subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and the housing 102. In such a configuration, a variety of different electrode support assemblies of varying shapes, sizes, and electrode configurations may be made available for physically and electrically connecting to a standard ITCS device.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst the subcutaneous electrodes 104.

Accordingly, dissection tools of the present invention may be shaped to provide appropriate access for specific electrodes or families of electrodes, electrode support assemblies, and/or leads. For example, a dissection tool of the present invention may be adapted to provide a chevron shaped tunnel, possibly having a particular radius of curvature, in order to facilitate placement of a semi-rigid chevron shaped curved electrode. Likewise, a kit may be assembled having particular shaped electrodes along with particular dissectors adapted for placement of the specific electrodes. The physician may use a number of specifically shaped dissection tools during an implant procedure. Depending on the configuration of a particular ITCS device, a delivery system incorporating drug/fluid delivery may advantageously be used to facilitate proper placement and orientation of the ITCS device housing and subcutaneous electrode(s).

Examples of tools, aspects of which may be incorporated into a dissecting tool in accordance with the present invention, are disclosed in commonly owned U.S. Pat. No. 5,300,106, U.S. Publication Nos. 2004/0204734 and 2004/0204735, which are hereby incorporated herein by reference. These and other conventional delivery devices may advantageously be modified to incorporate a drug/fluid delivery capability and other structural and functional features as described herein. An improved ITCS dissecting and device delivery tool in accordance with the present invention is described below.

Figure 2A:
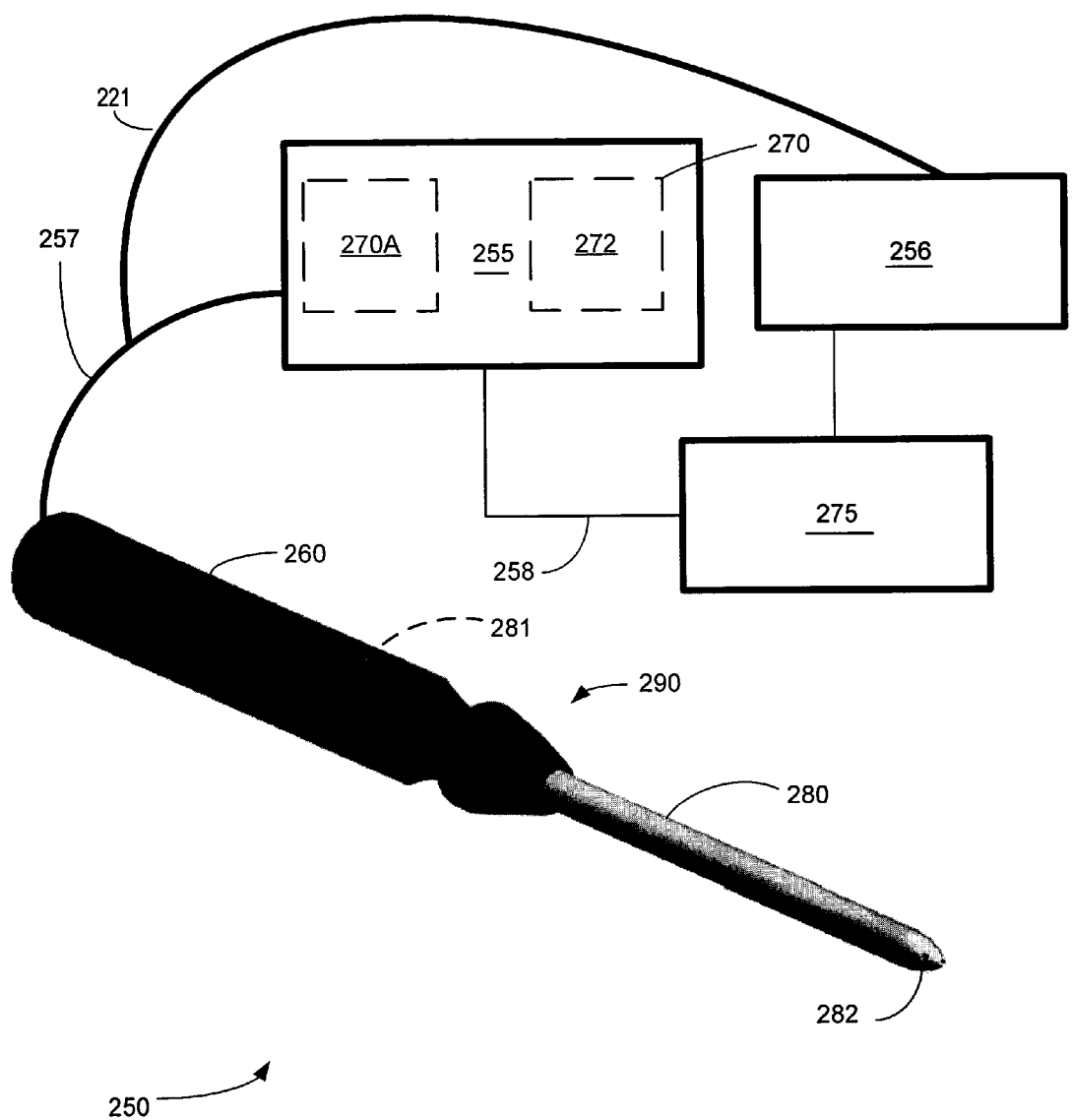
FIG. 2A is a perspective view of a subcutaneous dissection system in accordance with the present invention.
Figure 2B:
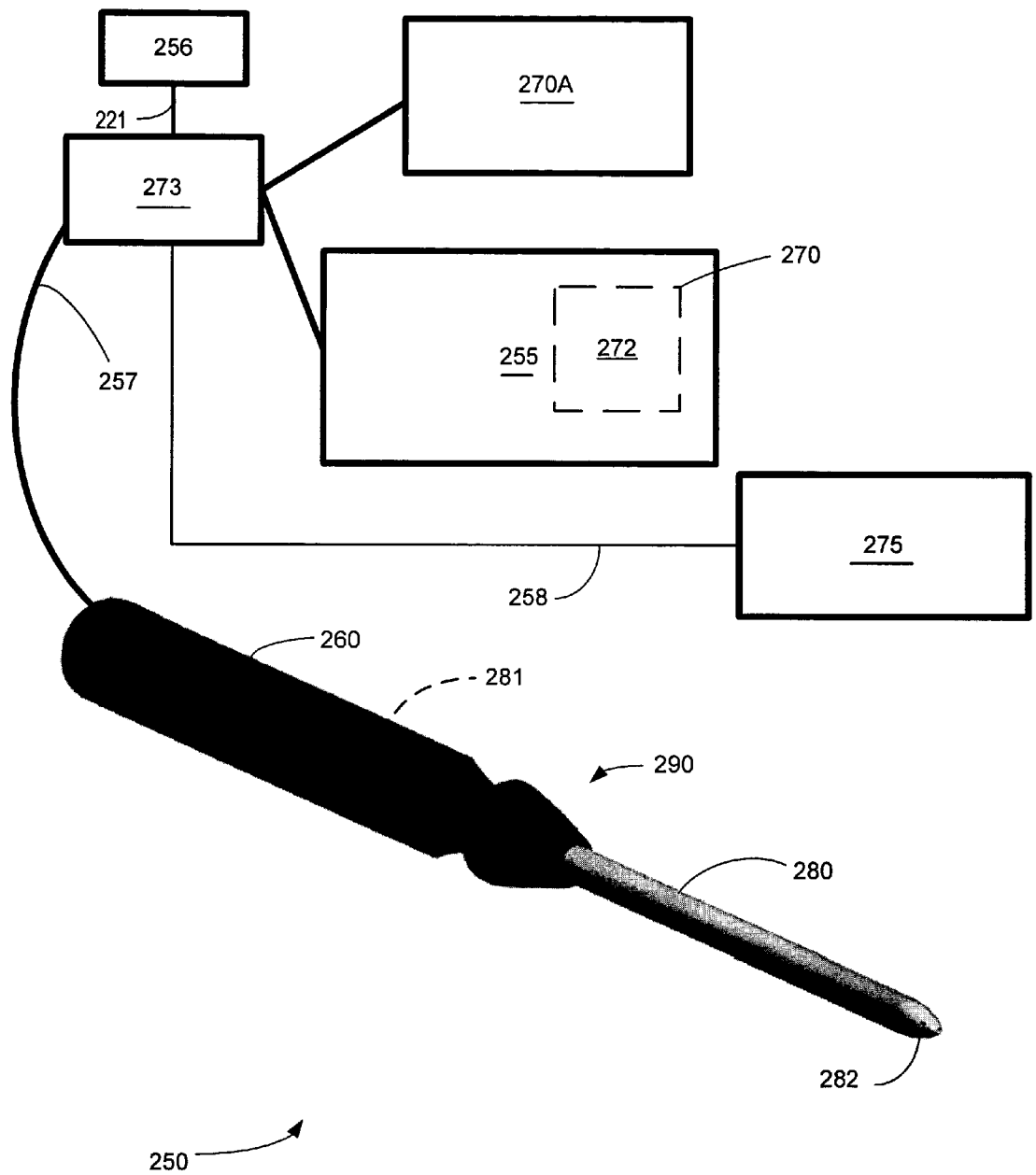
FIG. 2B is a perspective view of another subcutaneous dissection system in accordance with the present invention.

Embodiments of a delivery system according to the present invention are illustrated in FIGS. 2A and 2B. Referring to FIG. 2A, a subcutaneous dissection system 250 includes an ultrasonic generator 256 and a subcutaneous ultrasonic dissector 290 including a transducer 281, a handle 260 and an elongated dissecting member 280. The generator 256 is electrically coupled to the transducer 281 via a cable 221. A fluid, such as a pharmacological agent 272, is stored in a reservoir 270, and may be pumped by a pump 255 through a tubing 257 and delivered to tissue through a port system 282 of the subcutaneous ultrasonic dissector 290.

The pump 255 and generator 256 may be turned off and on using a control 275. The control 275 may be connected to the pump 255 and generator 256 by, for example, wiring 258. The control 275 may be, for example, a switch, a foot pedal, or other actuator capable of controlling the generator 256 and pump 255.

It may also be desirable to provide aspiration with the subcutaneous dissection system 250. An aspirant reservoir 270A may optionally be associated with the ultrasonic dissector 290. The aspirant reservoir 270A may be fluidly connected with the pump 255, whereby the pump 255 operates in a first mode to pump fluid into the subcutaneous ultrasonic dissector 290, and operates in a second mode to aspirate aspirant from the subcutaneous ultrasonic dissector 290. The aspirant reservoir 270A may also be connected to a vacuum system or other means of providing aspiration as is known in the art.

FIG. 2B is a perspective view of another subcutaneous dissection system in accordance with the present invention. In FIG. 2B, the aspirant reservoir 270A is connected to the subcutaneous ultrasonic dissector 290 through a valve 273. The pump 255 may also be fluidly connected to the subcutaneous ultrasonic dissector 290 through the valve 273. The valve 273 may be adapted to alternate between aspiration, irrigation, and/or fluid pumping modes. The tubing 257 may be a single lumen tubing, a multiple lumen tubing, or a multiple tube arrangement. The valve 273 may be adapted to provide simultaneous aspiration and pumping through a multiple lumen or multiple tubing arrangement. The valve 273 may be operated via actuation of the control 275.

The control 275 may be connected to the generator 256, the pump 255 and/or the valve 273 by, for example, wiring 258. The control 275 may be, for example, a switch, a foot pedal, or other actuator capable of controlling the generator 256, pump 255 and/or the valve 273. The control 275 may be, for example, a switch located on the handle 260, a foot pedal located within reach of a clinician's feet, or implemented within the pump 255 as a voice-activated solenoid actuated valve.

The pump 255 delivers the pharmacological agent 272 through tubing 257. Although the tubing 257 is illustrated as an element separate from the subcutaneous ultrasonic dissector 290, it is contemplated that some or all of the components illustrated in FIGS. 2A and 2B may be enclosed within the subcutaneous ultrasonic dissector 290, for example, within the handle 260. It is also contemplated that the tubing 257 may enter the subcutaneous ultrasonic dissector 290 distal to the handle 260, such as, for example, directly to the elongated dissecting member 280. It is further contemplated that the subcutaneous ultrasonic dissector 290 could be adapted to interface to a robotic surgical system by, for example, adapting the handle 260 to interface with a robotic arm instead of a clinician's hand.

Referring to FIGS. 2A and 2B, the pharmacological agent 272 may include any agent helpful to the efficacy of the subcutaneous ultrasonic dissector 290. The pharmacological agent 272 may include, for example, saline solution, phosphated buffer solution, an analgesic, an antibiotic, a hemostatic agent, an anti-inflammatory, or other useful drug or fluid.

For example, a non-exhaustive, non-limiting list of analgesics includes both fast acting and long acting drugs. PROCAINE, for example, may provide fast acting pain relief. BUPIVACAINE, LIDOCAINE, and MAPRIVACAINE, for example, may provide long acting pain relief.

A non-limiting example of a useful antibiotic is VANCOMYCIN, and a non-limiting example of an antiseptic in accordance with the present invention is CEFALOZIN. VANCOMYCIN may be used for the treatment of infection, and CEFALOZIN may be used to prevent possible infection along the dissection path.

A non-exhaustive, non-limiting list of anti-inflammatory drugs includes the glucocorticoid family of drugs (steroids). Useful anti-inflammatory drugs include DEXAMETHASONE, BETAMETHASONE, and IBUPROFIN, for example.

A non-exhaustive, non-limiting list of agents that may improve the electrical properties of dissected tissue includes the glucocorticoid family of drugs, including, for example, DEXAMETHASONE and BETAMETHASONE. These and other candidate drugs may provide for lower chronic defibrillation and pace/sense thresholds for subcutaneous lead/electrode systems. These and other fluids and/or drugs may be delivered individually or in desired combinations prior to, during, and after dissection for purposes of enhancing patient comfort, fighting infections, lowering defibrillation thresholds, and/or chemically treating other conditions.

In FIGS. 2A and 2B, the elongated dissecting member 280 is illustrated as a straight member. However, it is contemplated that the elongated dissection member 280 may have any useful shape. For example, the elongated dissecting member 280 may be curved in one or more planes, and may have a simple or complex curvature defined by one or more radii. The radii of curvature may range from about 25 cm to about 2.5 cm, for example.

The elongated dissecting member 280 may, for example, have a pre-defined curvature to properly position an ITCS electrode relative to the can for proper location of the electric field relative to a patient's heart. The elongated dissecting member 280 may also, or alternately, have a pre-defined curvature that may easily follow the curvature of the rib cage for proper dissection. It is contemplated that any combination of predefined shapes may be utilized in the present invention. It is also contemplated that multiple curvatures may also be used. For example, a first curvature in a first direction may help the ultrasonic dissector conform to the curvature of the rib cage, while a second curvature in a second direction may be useful for optimally locating the leads and can relative to the heart or other anatomy. As mentioned above, the curvature of the elongated dissecting member 280 may be defined by a single radius, or by multiple radii or varying radii.

Figure 3A:
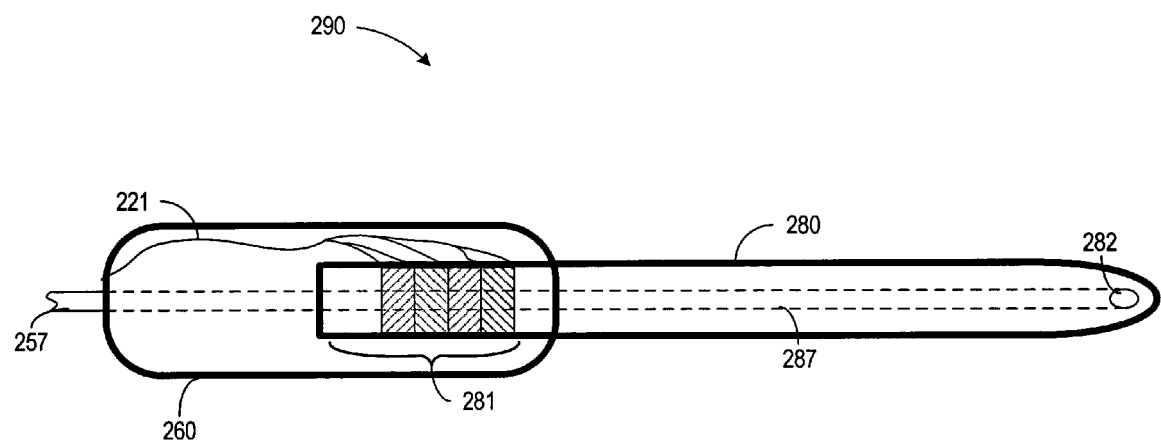
FIG. 3A is a plan view of an ultrasonic dissector in accordance with the present invention.
Figure 3B:
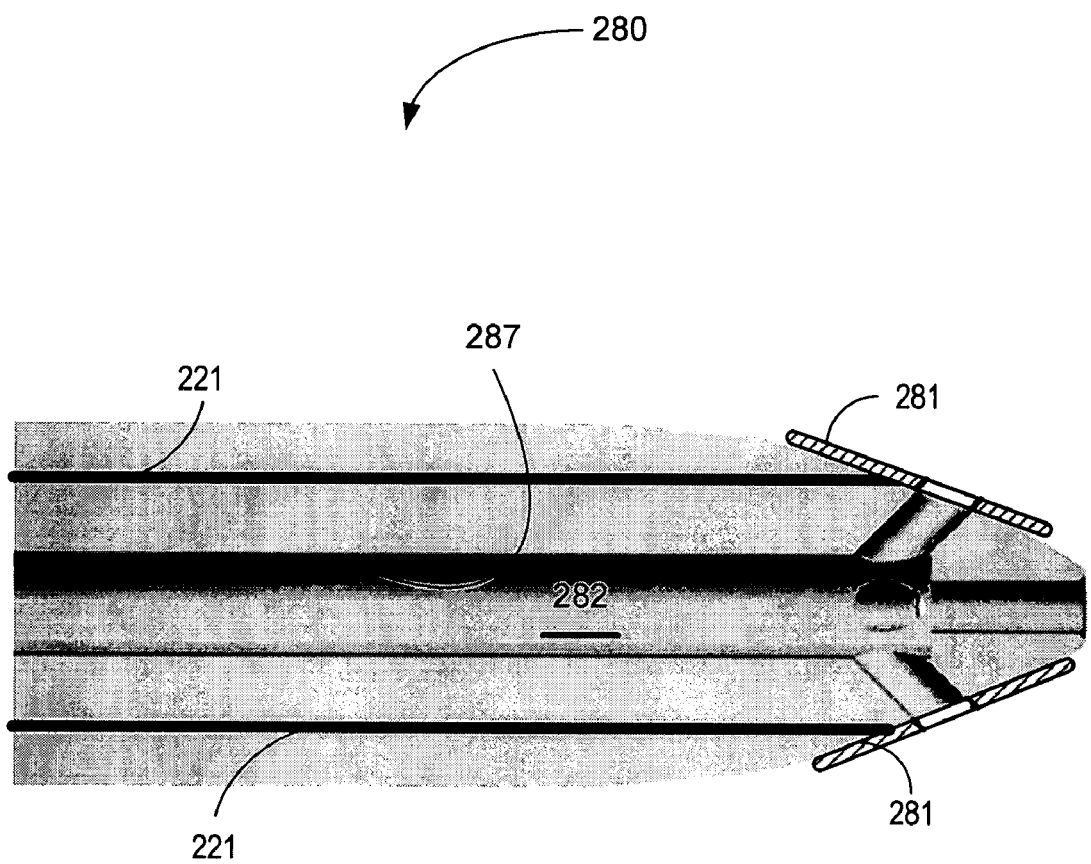
FIG. 3B is a magnified sectional view bisecting the distal end of an ultrasonic dissector in accordance with the present invention.
Figure 3C:
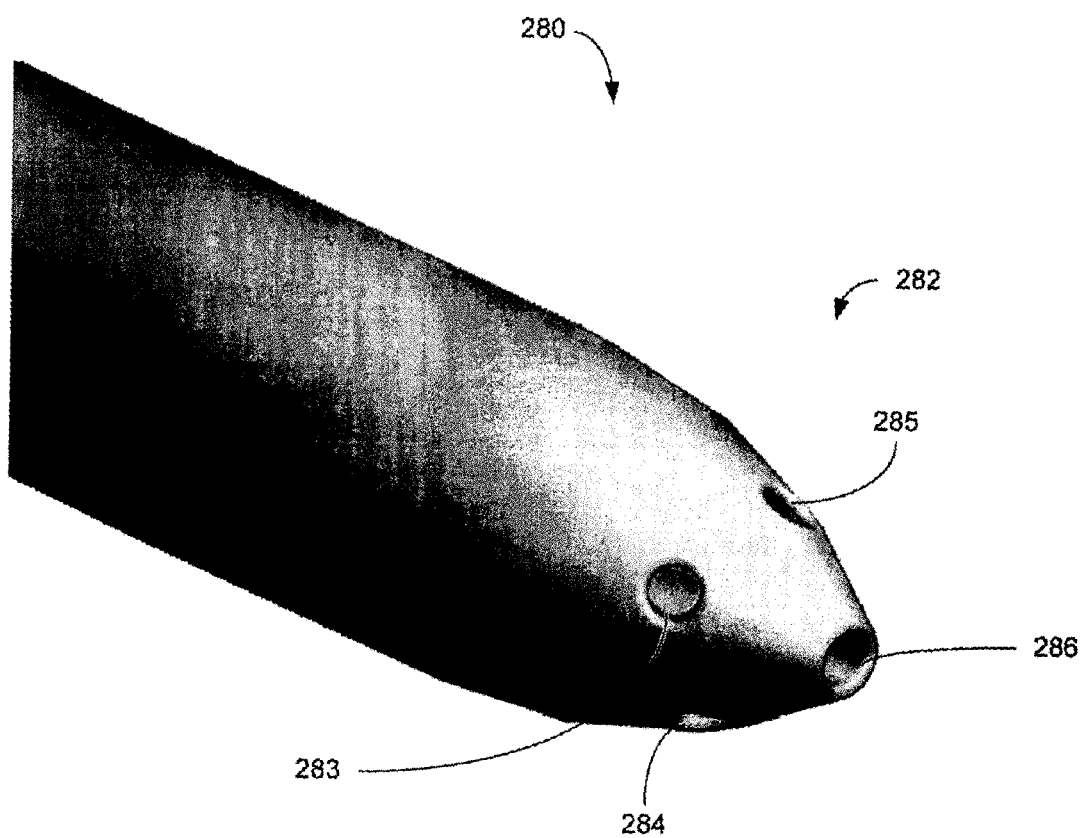
FIG. 3C is a magnified perspective view of the distal end of an ultrasonic dissector in accordance with the present invention.

FIGS. 3A through 3C illustrate various embodiments of subcutaneous ultrasonic dissector 290 and dissecting element 280 in accordance with the present invention. FIG. 3A illustrates an embodiment of the subcutaneous ultrasonic dissector 290 having the ultrasonic transducer 281 proximal of the elongated dissecting element 280, an arrangement suitable for low-frequency high-power applications such as, for example, below 200 kilohertz, and particularly within the range of about 20 kilohertz to about 50 kilohertz.

The ultrasonic transducer 281 converts electrical energy from the generator 256 (shown in FIGS. 2A and 2B) to mechanical motion of the elongated dissecting member 280. The mechanical motion disrupts tissue as the elongated dissecting member 280 is inserted, facilitating the dissection. For example, the elongated dissecting member 280 may liquefy adipose tissue, creating a tunnel for subsequent lead placement. Transducers of this type are known in the art, such as, for example, U.S. Pat. No. 5,449,370, hereby incorporated herein by reference. The mechanical motion is also useful for driving the pharmacological agent into tissue, a process often referred to as sonophoresis.

FIG. 3B illustrates an embodiment of the elongated dissecting element 280 having the ultrasonic transducer 281 at the distal end, an arrangement particularly suitable for high-frequency high-power applications. The ultrasonic transducer 281 converts electrical energy from the generator 256 to pressure-waves that emanate from the ultrasonic transducer 281. This arrangement is effective for frequencies above 200 kilohertz and in megahertz ranges, particularly in the range of about 1 megahertz to about 4 megahertz. Transducers of this type are known in the art, such as, for example, U.S. Pat. Nos. 7,135,029 and 6,500,121, which are hereby incorporated herein by reference. The pressure waves, similarly to the mechanical motion described above, are useful for sonophoresis.

Referring to FIGS. 3A and 3B, the ultrasonic transducer 281 may be driven continuously, or may also be modulated or interrupted. For example, the ultrasonic transducer 281 may be driven at a duty cycle having a first amplitude for a portion of the cycle, and having effectively zero amplitude for the remainder of the cycle. The ultrasonic transducer 281 may also be driven at varying amplitudes over a cycle in a modulated mode, such as, for example, having a saw-tooth modulation envelope or other envelopes as is known in the art. A convenient measure of system power is the power transferred from the generator 256 to the transducer 281. System power may vary between about 1 Watt and about 200 Watts.

FIG. 3C is a magnified perspective view of the distal end of the elongated dissecting element 280 shown in FIGS. 2A and 2B. A port system 282 is depicted as having an axial aperture 286 and a number of lateral apertures 283, 284, and 285. Depiction of the apertures 283, 284, 285 and 286 is for purposes of clarity of explanation, and not of limitation. It is contemplated that a single aperture, or any number of apertures, may be located on the elongated dissecting element 280 at any location.

For example, a single or series of apertures may be located proximally from the distal end of the elongated dissecting member 280 to provide a pharmacological agent or other fluid anywhere along the path of dissection. If, for example, an analgesic is delivered during dissection, it may be efficacious to provide a number of ports of port system 282 at the distal end of the ultrasonic dissector to ease the pain of dissection, but also to deliver incremental amounts of analgesic along the length of the elongated dissecting member 280 as the ultrasonic dissector advances into tissue.

The pharmacological agent 272 (shown in FIGS. 2A and 2B) may be delivered continuously from the port system 282 during dissection. It is also contemplated that the pharmacological agent 272 may be delivered in bolus fashion at time intervals, or only delivered on demand through actuation of the control 275. For example, the pharmacological agent 272 may be delivered when a clinician desires to flush out debris from the dissection path, and may deliver saline solution to remove the debris. As the pharmacological agent 272 is delivered from the subcutaneous ultrasonic dissector 290, the ultrasonic energy may drive the agent into the tissue surrounding the elongated dissecting member 280.

Figure 4:
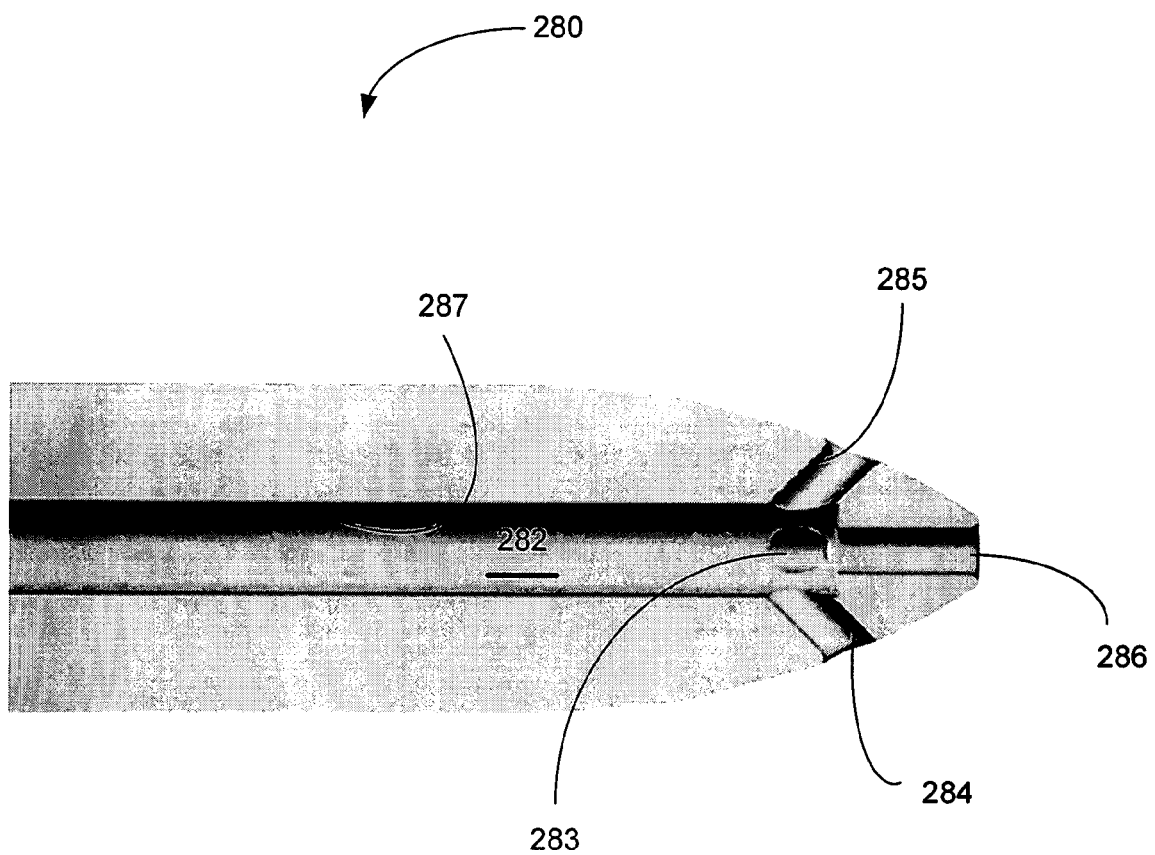
FIG. 4 is a magnified sectional view bisecting the distal end of an ultrasonic dissector in accordance with the present invention.

FIG. 4 is a magnified sectional view bisecting the distal end illustrated in FIG. 3C. In FIG. 4, the port system 282 is illustrated as including a single channel 287 terminating in the port system 282. Apertures 283, 284, 285, and 286 are fluidly coupled to the channel 287 via branch channels to provide an exit point for a pharmacological or other fluid. The channel 287 may be, for example, molded or machined from Titanium, such as, for example, Ti6Al4V or other suitable material. For example, the elongated dissecting element 280 may be machined from a suitable material, and include one or more channels 287. The elongated dissecting member 280 may include a number of channels 287 terminating in a number of port systems 282 to provide delivery of a variety of fluids and/or pharmacological agents 272, and/or to provide delivery of fluids and/or pharmacological agents 272 to different locations along the length of the elongated dissecting member 280.

Figure 5:
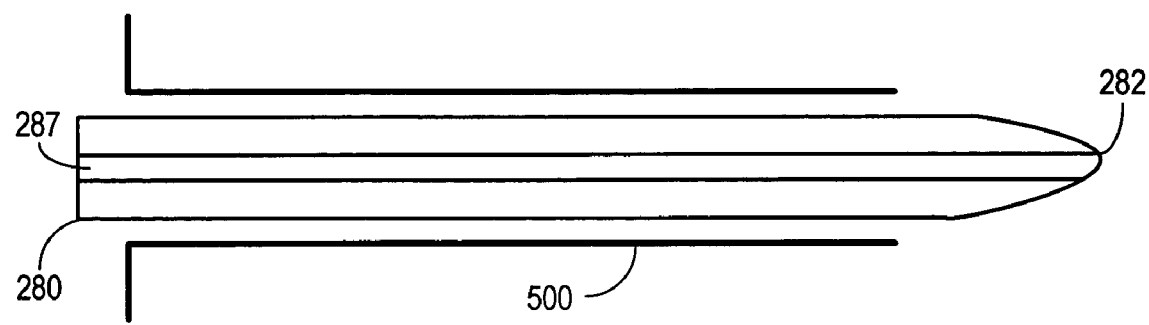
FIG. 5 is a section view of the elongated dissecting member of an ultrasonic dissector having a surrounding sheath in accordance with the present invention.

Referring now to FIG. 5, a sheath 500 may be provided to surround the elongated dissecting member 280. The sheath 500 may extend along a portion of, or the entire length of, the elongated dissecting member 280. As dissection occurs, the sheath 500 may be inserted along the dissection path. Alternatively, the sheath 500 may be inserted after the dissection procedure is completed. Upon completion of the dissection procedure, the subcutaneous ultrasonic dissector 290 may be removed from the patient's body. After removal of the subcutaneous ultrasonic dissector 290, the sheath 500 may be left in-place, to provide a guide for placement of electrodes and/or the ITCS housing. After placement of the electrodes and/or housing, the sheath 500 may be stripped out, leaving the electrodes properly positioned.

In one embodiment, the sheath 500 may include one or more longitudinal pre-stress lines extending between a distal end and a proximal end of the sheath 500. The sheath 500 may optionally include a sheath handle. The pre-stress line provides for a peel-away or tear-away sheath 500 that facilitates extraction of the sheath 500 from the body. If the sheath 500 is provided with a sheath handle, the sheath handle is preferably separable into at least two sections such that sheath handle separation splits the sheath along the longitudinal pre-stress line at the proximal end of the sheath 500. The sheath 500 (with or without a sheath handle) splits along the longitudinal pre-stress line upon sheath retraction in a proximal direction.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A dissection tool, comprising:
   an elongated handle having a proximal end and a distal end;
   an elongated dissecting element having a proximal end and a tapered distal end, the proximal end of the elongated dissecting element coupled to the handle and the elongated dissecting element extending from the distal end of the handle;
   two ultrasonic transducers provided along the tapering of the distal end of the elongated dissecting element, the ultrasonic transducers provided on opposite sides of the elongated dissecting element; and
   a fluid channel system extending from at least the proximal end of the elongated dissecting element to the distal end of the elongated dissecting element, the fluid channel system terminating in a port system having a plurality of apertures along the tapering of the distal end of the elongated dissecting element.

2. The dissection tool of claim 1, wherein the ultrasonic transducers are driven by a signal at one or more frequencies ranging between about 0.2 megahertz and about 3 megahertz.

3. The dissection tool of claim 1, wherein the ultrasonic transducers are driven by a pulsed electrical signal having a duty cycle ranging between about 10% and 100%.

4. The dissection tool of claim 1, wherein the ultrasonic transducers are driven at a power level ranging between about 1 watt and about 200 watts.

5. The dissection tool of claim 1, wherein the port system comprises a plurality of apertures.

6. The dissection tool of claim 1, wherein at least one of the ultrasonic transducers comprises a hole and the at least one ultrasonic transducer is positioned on the tapering of the distal end of the elongated dissecting element such that the hole of the ultrasonic transducer is aligned with an aperture of the plurality of apertures to allow fluid flow through the aperture and the hole.

7. The dissection tool of claim 1, wherein the plurality of apertures of the port system comprises at least two lateral apertures non-coincident with the longitudinal axis of the elongated dissecting element and an axial aperture coincident with the longitudinal axis of the elongated dissecting element and terminating a distal tip of the elongated dissecting element, and wherein each of the two ultrasonic transducers respectively comprises a hole and each ultrasonic transducer is positioned on the tapering of the distal end of the elongated dissecting element such that each hole of each ultrasonic transducer is aligned with different lateral apertures of the port system to allow fluid flow through the lateral apertures and the holes.

8. The dissection tool of claim 1, further comprising a delivery system having a pump, an irrigation fluid reservoir, and a pharmacological agent reservoir, wherein the dissection tool is configured to deliver irrigation fluid from the irrigation fluid reservoir through the fluid channel system and out at least one aperture of the plurality of apertures of the port system and deliver pharmacological agent from the pharmacological agent reservoir through the fluid channel system and out at least one other aperture of the plurality of apertures of the port system.

9. A dissection tool, comprising:
   at least two ultrasonic transducers;
   means, coupled to the ultrasonic transducers, for dissecting subcutaneous tissue employing an elongated dissecting element having a proximal end and a tapered distal end, the ultrasonic transducers coupled to the elongated dissecting element such that the ultrasonic transducers vibrates the elongated dissecting element to facilitate tissue dissection; and
   means for delivering a fluid through or along the elongated dissecting element of the dissecting means and to tissue subject to dissection, the fluid exiting the dissection tool through a port system having a plurality of apertures along the tapering of the distal end of the elongated dissecting element, wherein the at least two ultrasonic transducers are provided along the tapered distal end of the elongated dissecting element and the at least two ultrasonic transducers are provided on opposite sides of the elongated dissecting element.

10. The dissection tool of claim 9, further comprising means for controllably supplying the fluid to the fluid delivering means.

11. The dissection tool of claim 9, further comprising means for aspirating debris from the dissected tissue.

12. The dissection tool of claim 9, wherein at least one of the ultrasonic transducers is mounted on the tapering of the distal end of the elongated dissecting element and over at least one of the apertures of the plurality of apertures such that a hole in the at least one ultrasonic transducer is aligned with the at least one aperture to allow fluid flow through the at least one aperture and the hole.

13. The dissection tool of claim 9, further comprising means for impelling the fluid from the dissecting means and into the tissue subject to dissection employing sonophoresis.

* * * * *